(12) United States Patent
Ishihara et al.

(10) Patent No.: US 6,844,098 B1
(45) Date of Patent: Jan. 18, 2005

(54) OXIDE-ION CONDUCTOR AND USE THEREOF

(75) Inventors: Tatsumi Ishihara, 959-22 Oshino, Oita-shi, Oita 870-1121 (JP); Yusaku Takita, 3-4-33 Miyazakidai, Oita-shi, Oita 870-1137 (JP)

(73) Assignees: Mitsubishi Materials Corporation, Tokyo (JP); Tatsumi Ishihara, Oita (JP); Yusaku Takita, Oita (JP)

( * ) Notice: Subject to any disclaimer, the term of this patent is extended or adjusted under 35 U.S.C. 154(b) by 0 days.

(21) Appl. No.: 09/144,217

(22) Filed: Aug. 31, 1998

(30) Foreign Application Priority Data

Aug. 29, 1997 (JP) .............................................. 9-9234838
Mar. 26, 1998 (JP) ............................................ 10-079583
Mar. 27, 1998 (JP) ............................................ 10-081185

(51) Int. Cl.$^7$ ............................................... H01M 8/10
(52) U.S. Cl. .......................... 429/33; 429/30; 73/23.35; 205/782.5; 468/437
(58) Field of Search ..................... 429/30, 33; 73/23.35; 205/782.5; 468/437

(56) References Cited

U.S. PATENT DOCUMENTS 4,594,297 A * 6/1986 Polak et al. .................. 429/13

* cited by examiner

*Primary Examiner*—Maria Nuzzolillo
*Assistant Examiner*—M. Wills
(74) *Attorney, Agent, or Firm*—Oblon, Spivak, McClelland, Maier & Neustadt, P.C.

(57) ABSTRACT

An oxide-ion conductor has the formula $Ln_{1-x}A_xGa_{1-y-x}B1_yB2_z$ oxide, wherein Ln is at least one element selected from the group consisting of La, Ce, Pr, Nd and Sm; A is at least one element selected from the group consisting of Sr, Ca and Ba; B1 is at least one element selected from the group consisting of Mg, Al and In; B2 is at least one element selected from the group consisting of Co, Fe, Ni and Cu; x is 0.05 to 0.3; y is 0 to 0.29; z is 0.01 to 0.3; and y+z is 0.025 to 0.3. The oxide-ion conductor exhibits higher oxide-ion conductivity than stabilized zirconia, excellent heat resistance and also high ion conductivity even at low temperatures, as well as exhibiting low oxygen-partial-pressure dependence of ion conductivity.

43 Claims, 8 Drawing Sheets

OXIDE-ION CONDUCTOR AND USE THEREOF

BACKGROUND OF THE INVENTION

1. Field of the Invention

The present invention relates to a novel rare earth gallate oxide-ion conductor, having a perovskite structure. The oxide-ion conductor of the present invention exhibits very high oxide-ion conductivity or oxide-ion mixed conductivity without being substantially affected by oxygen partial pressure, and can effectively be incorporated in an electrolyte of a fuel cell, an air electrode of a fuel cell, a gas sensor such as oxygen sensor, an oxygen separating film such as electrochemical oxygen pump, a gas separator membrane, and so forth.

2. Discussion of the Background

An oxide-ion conductor owes its electrical conductivity mainly to the mobility of oxide ions ($O^{2-}$), without substantially relying on conductivity by electrons. In general, such an oxide-ion conductor is made of a metal oxide that is doped with another metal, so as to generate $O^{2-}$ vacancies. Attempts have been made to put such oxide-ion conductors to use in various types of materials, such as electrolytes of solid oxide (solid electrolyte) fuel cells (SOFC), gas sensors, e.g., oxygen sensors, and oxygen separator membranes of electrochemical oxygen pumps.

A typical example of such oxide-ion conductors are cubic fluorite type solid-solutions referred to as "stabilized zirconia" composed of zirconium oxide ($ZrO_2$) containing a small quantity of dissolved divalent or trivalent metal oxide, such as CaO, MgO, $Y_2O_3$, $Gd_2O_3$ or the like. The stabilized zirconia excels in heat resistance, and has conductivity that is predominantly provided by oxide ions over the entire range of oxygen partial pressure, i.e., from a pure oxygen atmosphere to a hydrogen atmosphere. Thus, the stabilized zirconia is less liable to exhibit reduction in the ion transference number (the ratio of conductivity given by the oxide ions to the overall conductivity), even under reduced oxygen partial pressure.

Zirconia oxygen sensors made of the stabilized zirconia are used for various purposes, such as control of industrial processes including steel making, air-fuel ratio control of automotive engines, and so forth. The stabilized zirconia is also used as the material of a solid oxide fuel cell (SOFC) which is being developed and which operates at temperatures around 1000° C. It is to be noted, however, that the oxide-ion conductivity of stabilized zirconia is not so high, and tends to cause insufficiency of electrical conductivity when the temperature is lowered. For instance, the ion conductivity of a $Y_2O_3$ stabilized zirconia exhibits an ion conductivity which is as high as $10^{-1}$ S/cm at 1000° C. but is reduced to $10^{-4}$ S/cm when the temperature is lowered to 500° C. This stabilized zirconia, therefore, is usable only at high temperatures not lower than 800° C.

Fluorite type compounds exhibits a very high oxide-ion conductivity exceeding that of stabilized zirconia. An example of such a fluorite type compound is a $Bi_2O_3$-type oxide composed of $Bi_2O_3$ containing dissolved $Y_2O_3$ in the form of a solid solution. Such a fluorite type compound, however, has a low melting point of 850° C. or less, thus exhibiting inferior resistance to heat, although it exhibits very high levels of ion conductivity. In addition, the fluorite type compounds is not resistant to a reducing atmosphere. More specifically, when the oxygen partial pressure are lowered, n-type electron-based electrical conductivity prevails due to a change in the oxidation state of $Bi^{3+}$ to $Bi^{2+}$. A further reduction in the oxygen partial pressure to a level approximating a pure hydrogen atmosphere causes the compound to be reduced to the metal. The fluorite type compounds, therefore, cannot be used as a material for fuel cells.

Another kind of known fluorite type oxide-ion conductor is a $ThO_2$ type oxide. This oxide exhibits oxide-ion conductivity much smaller than that of stabilized zirconia. In addition, electron-based electrical conduction becomes dominant so as to markedly lower the ion transference number, particularly under low oxygen partial pressures. A $CeO_2$ type oxide, although it exhibits oxide-ion conductivity exceeding that of stabilized zirconia, permits n-type electron-based electrical conduction to prevail due to a change in the oxidation state of $Ce^{4+}$ to $Ce^{3+}$ when the oxygen partial pressure is reduced to $10^{-12}$ atm or less. Consequently, reduction of the ion transference number is also unavoidable with this type of compound.

Oxide-ion type conductors are also known that have crystalline structures other than the fluorite structure. Examples of such oxide-ion type conductors are $PbWO_4$, $LaAlO_3$, $CaTiO_3$ and so forth. These conductors, however, do not have high oxide-ion conductivity and, under low oxygen partial pressure, allow semi-conduction to appear so that electron-based electrical conduction prevails, resulting in a low ion transference number.

SUMMARY OF THE INVENTION

As discussed in the foregoing, although oxide-ion conductors having higher oxide-ion conductivity than stabilized zirconia are known, such known conductors cannot suitably be used as the material of an electrolyte in solid oxide fuel cells, oxygen sensors and so forth, because of insufficiency in heat resistance and/or a large reduction in the ion transference number due to prominence of electrical conductivity provided by electrons.

Accordingly, an object of the present invention is to provide an oxide-ion conductor that has superior characteristics, such as oxide-ion conductivity greater than that of stabilized zirconia, superb heat resistance, and high oxide-ion conductivity not only at high temperatures but at low temperatures as well. Preferably, the oxidation conductor exhibits only a small reduction in the ion transference number, i.e., prominence of electrical conduction by oxide ions, over the entire range of oxygen partial pressure from that of a pure oxygen atmosphere to that of a hydrogen atmosphere, i.e., even when the oxygen partial pressure is lowered, or provide a high mixed ion conductor.

The inventors conducted an intense study to achieve the above-described object, and found that a material having high oxide-ion conductivity is obtained from rare earth gallate oxides having the perovskite structure expressed by AB03 (wherein A is one, two or more lanthanoide-type rare earth metal(s), and B is Ga), by substituting part of the rare earth metal of the A site with an alkaline earth metal and/or substituting part of Ga atoms of the B site with a non-transition metal such as Mg, In or Al. The inventors found that a particularly high level of oxide-ion conductivity is exhibited by a compound which has the formula $La_{0.8}Sr_{0.2}Ga_{0.8}Mg_{0.2}O_{3-w}$.

FIG. 1 is a graph showing the electrical conductivity of this compound in comparison with that of conventional oxide-ion conductors. From this graph, it will be seen that the compound $La_{0.8}Sr_{0.2}Ga_{0.8}Mg_{0.2}O_{3-w}$ exhibits superior electrical conductivity than those exhibited by $Y_2O_3$ stabilized zirconia and CaO stabilized zirconia, that are typical conventional zirconias. $Bi_2O_3$ type oxides exhibit electrical conductivity higher than that of the above-mentioned compound, but cannot practically be used as an oxide-ion conductor, because of the aforesaid shortcomings such as insufficiency of heat resistance and small resistance to reducing atmospheres.

The inventors have made a study to find materials which would exhibit still higher oxide-ion conductivity. As a result, the inventors have discovered that the addition of a small amount of a transition metal to the B site of the aforesaid rare earth gallate oxide provides a further improvement in the oxide-ion conductivity, thus offering satisfactorily high oxide-ion conductivity even at low temperatures.

Thus, according to the present invention, there is provided an oxide-ion conductor having the formula (1):

$$Ln_{1-x}A_xGa_{1-y-z}B1_yB2_zO_{3-w} \qquad (1)$$

wherein,

Ln is one, two or more elements selected from the group consisting of La, Ce, Pr, Nd and Sm;

A is one, two or more elements selected from the group consisting of Sr, C a and Ba;

B1 is one, two or more elements selected from the group consisting of Mg, Al and In; and B2 is one, two or more elements selected from the group consisting of Co, Fe, Ni and Cu; and wherein the following conditions are met:

x is 0.05 to 0.3;

y is 0 to 0.29;

z is 0.01 to 0.3; and y+z is 0.025 to 0.3; and w corresponds to the number of oxide ion vacancies. This oxide ion conductor may also be referred to as $Ln_{1-x}A_xGa_{1-y-z}B1_yB2_z$ oxide.

In the description of the present invention, the term "oxide-ion conductor" is used to mean electrical conductive materials that exhibit substantial oxide-ion conductivity. Thus, the term "oxide-ion conductor" covers not only oxide-ion conductors in the narrower sense in which most of the electrical conductivity is constituted by oxide-ion conductivity, but also materials of a broader sense including materials referred to as "electron-ion mixed conductors" (referred to also as "oxide-ion-mixed conductors") in which both the conduction of electrons and the conduction of oxide ions constitute substantial parts of the total conduction.

In the case of the oxide-ion conductors in the narrower sense in which most of electrical conductivity is constituted by oxide-ion conductivity, the ion transference number (ratio of the electrical conductivity provided by oxide-ion conductivity to the total conductivity) is preferably 0.7 or greater, and more preferably 0.9 or greater. In case of electron-ion mixed conductor, the ion transference number preferably ranges from 0.1 to 0.7, more preferably from 0.2 to 0.6.

The present invention also provides a solid oxide fuel cell (SOFC) in which the above-mentioned oxide-ion conductor is used as the electrolyte or as the air electrode, a gas sensor using the above-mentioned oxide-ion conductor, an oxygen separator membrane of an electrochemical oxygen pump using the above-mentioned oxide-ion conductor, and a gas separator membrane made of the above-mentioned oxide-ion conductor that functions owing to a difference in gas concentration.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

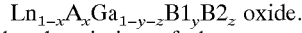

Figure 8:
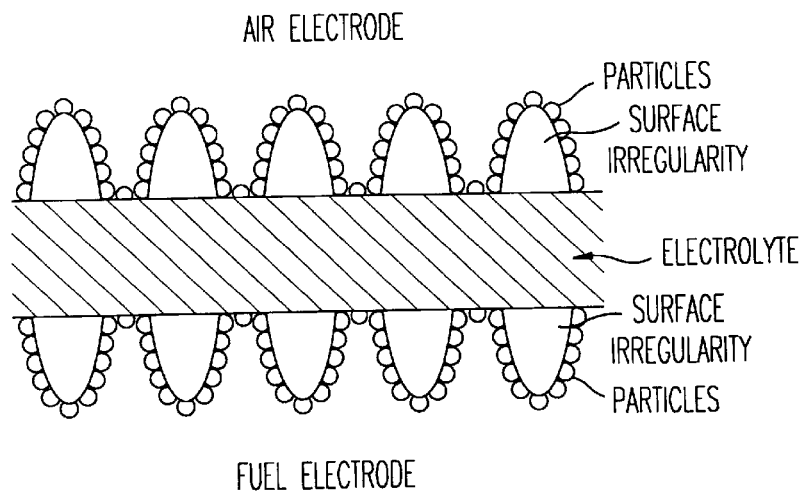
FIG. 8 is a schematic cross-sectional view of a solid oxide fuel cell having convex and concave surface portions.

FIG. 9 is an illustration of an interface between an electrolyte layer and an air electrode in the cell structure shown in FIG. 8.

Figure 10:
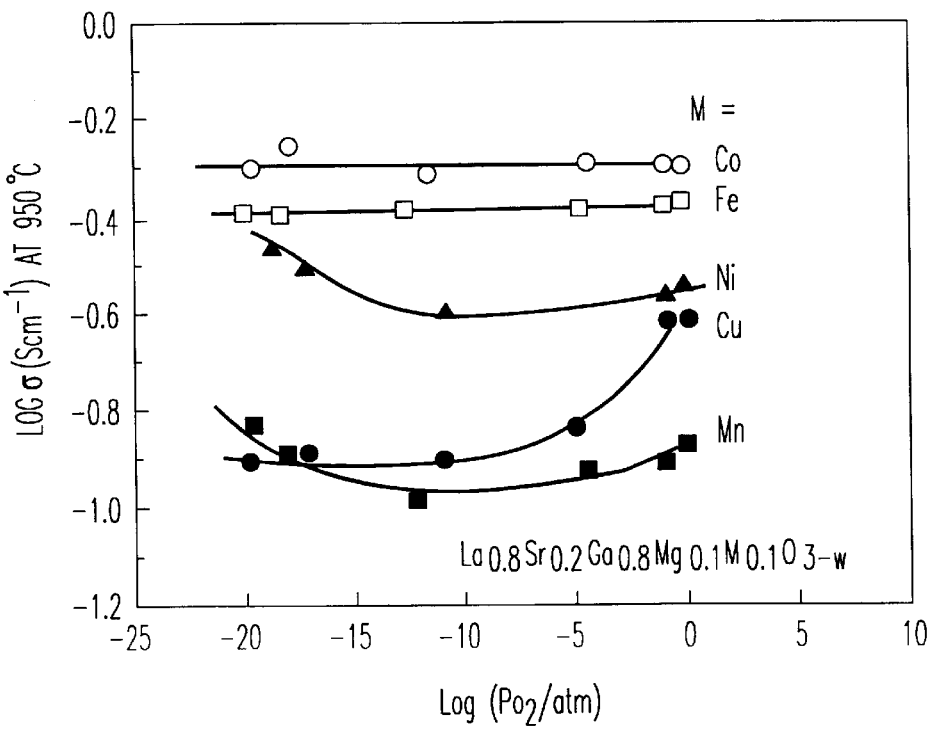

FIG. 10 is a graph showing dependence on oxygen partial pressure of the electrical conductivity of an oxide-ion conductor of the invention of a 5-element compound oxide.

Figure 11:
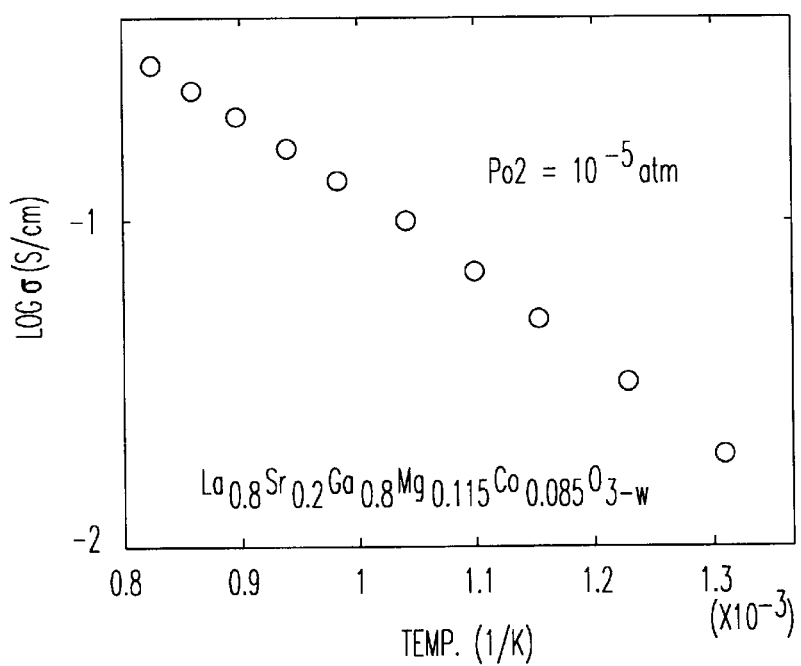

FIG. 11 is a graph showing dependence on temperature of the electrical conductivity of another oxide-ion conductor of the invention of a 5-element compound oxide.

Figure 12A:
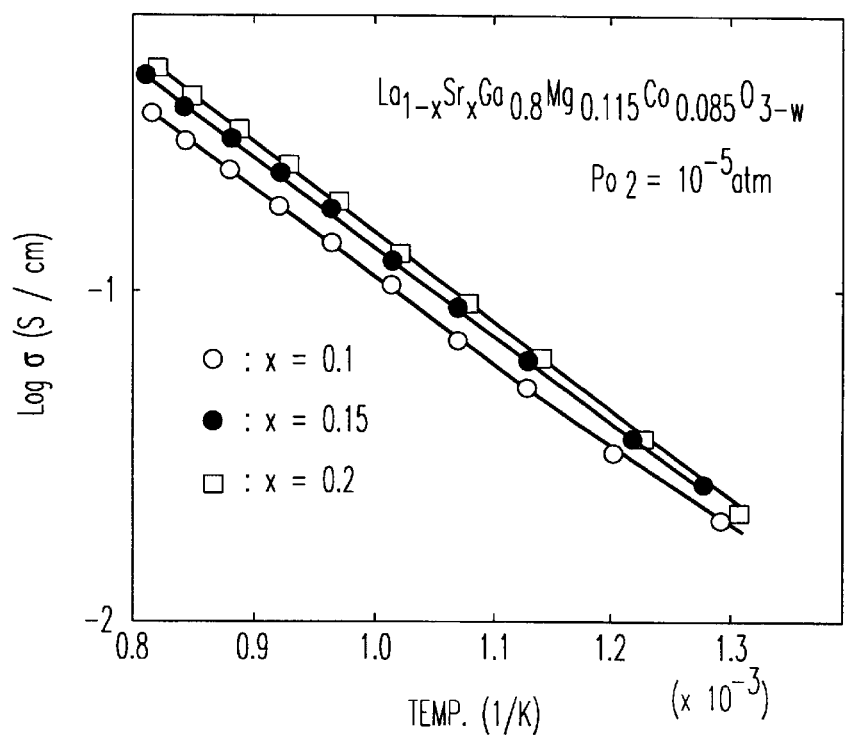

FIG. 12A is a graph showing dependence on temperature of the electrical conductivity of a different oxide-ion conductor of the invention of a 5-element compound oxide.

Figure 12B:
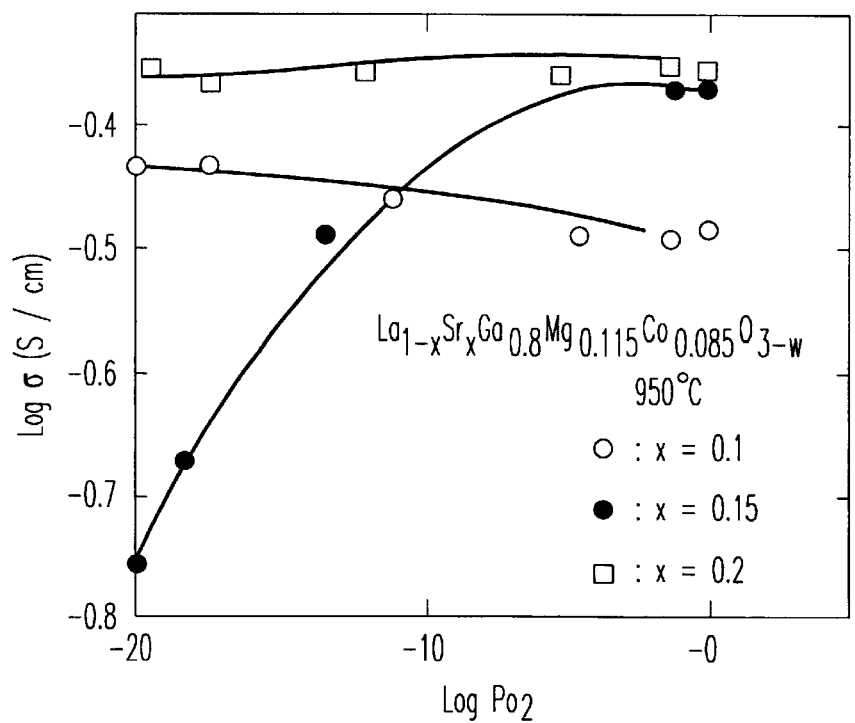

FIG. 12B is a graph showing dependence on oxygen partial pressure of the electrical conductivity of the different oxide-ion conductor of the invention of a 5-element compound oxide.

DETAILED DESCRIPTION OF THE INVENTION

The oxide-ion conductor in accordance with the invention, having a composition expressed by the formula (1), has a perovskite structure $ABO_3$, wherein the A site is occupied by the Ln atoms and A atoms of the formula (1), while the B site is occupied by the remainder Ga atoms, B1 atoms and B2 atoms. It is to be noted that the B1 atoms are not essential and may be dispensed with.

In accordance with the invention, part of the A site and part of the B site, that are typically occupied by trivalent metals, are occupied by divalent metals (e.g., the A atoms occupying part of the A site and Mg as B1 of the B site) or with transition metals (e.g., B2 atoms as part of the B site), whereby oxygen vacancies are formed. Oxide ion conductivity appears as a result of generation of these oxygen vacancies. Obviously, the number of oxygen atoms decreases by an amount corresponding to the number of the oxygen vacancies.

More specifically although the formula (1) indicates that the maximum number of oxygen atoms is 3, this number is actually 3 or less. The number of the oxygen vacancies, however, is dependent not only on the kinds of the atoms added (e.g., A, B1, B2), but also on other factors such as the temperature, oxygen partial pressure, kinds and quantity of the B2 atoms, and so forth. Therefore, the number of oxygen holes at any moment is dependent on extrinsic factors, and is not a fixed number.

In the formula (1), Ln is a lanthanoid-type rare earth metal, A is an alkaline earth metal, B1 is a non-transition metal and B2 is a transition metal. Thus, the oxide-ion conductor in accordance with the present invention is obtained by preparing lanthanoid gallate ($LnGaO_3$) as the basic structure and doping the lanthanoid gallate with three kinds of elements: an alkaline earth metal (A), a non-transition metal (B1) and a transition metal (B2) or, alternatively, with two kinds of elements: an alkaline earth metal (A) and a transition metal (B2). Thus, the oxide-ion conductor of the present invention is obtained either in the form of a 5-element compound oxide (Ln+A+Ga+B1+B2) or a 4-element compound oxide (Ln+A+Ga+B2). These compound oxides will be collectively referred to as "5/4-element compound oxides".

Figure 1:
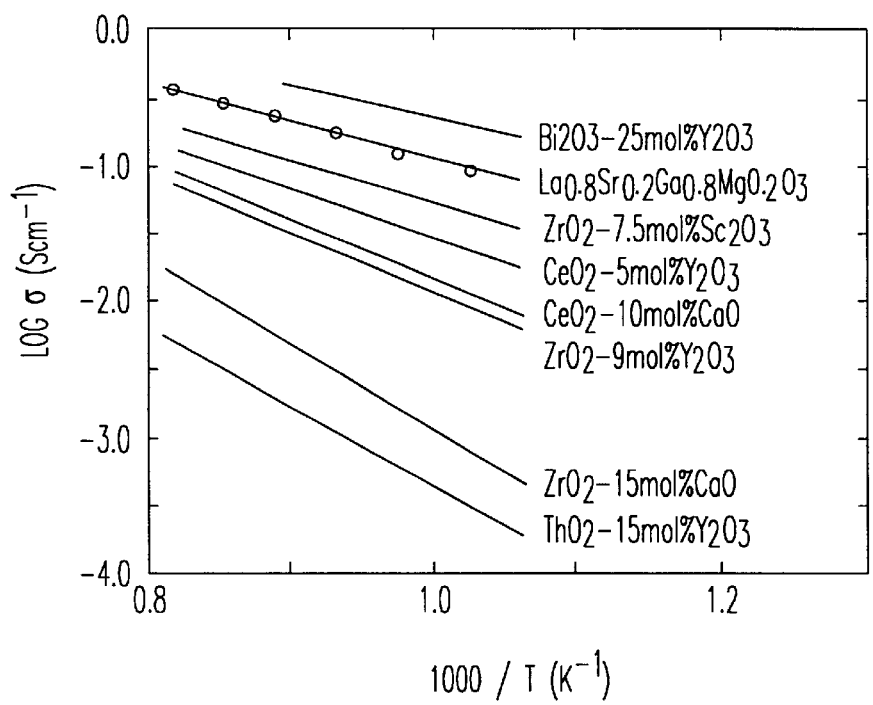
FIG. 1 is a graph showing electrical conductivity of a typical conventional oxide-ion conductor and that of a 4-element compound oxide having a perovskite crystalline structure and expressed by $La_{0.8}Sr_{0.2}Ga_{0.8}Mg_{0.2}O_{3-w}$.

A 4-element compound oxide of Ln+A+Ga+B1, a typical example of which is the above-mentioned $La_{0.8}Sr_{0.2}Ga_{0.8}Mg_{0.2}O_{3-w}$ also is an excellent oxide-ion conductor that exhibits higher oxide ion conductivity than stabilized zirconia, as can be seen from FIG. 1. This 4-element compound oxide will be referred to as a "reference 4-element compound oxide". In accordance with the present invention, substitution of a part or the whole of the B1 atoms of the reference 4-element compound oxide with a transition metal (B2 atoms) provides an oxide-ion conductor which in general exhibits a higher oxide ion conductivity than the reference 4-element compound oxide.

Figure 2:
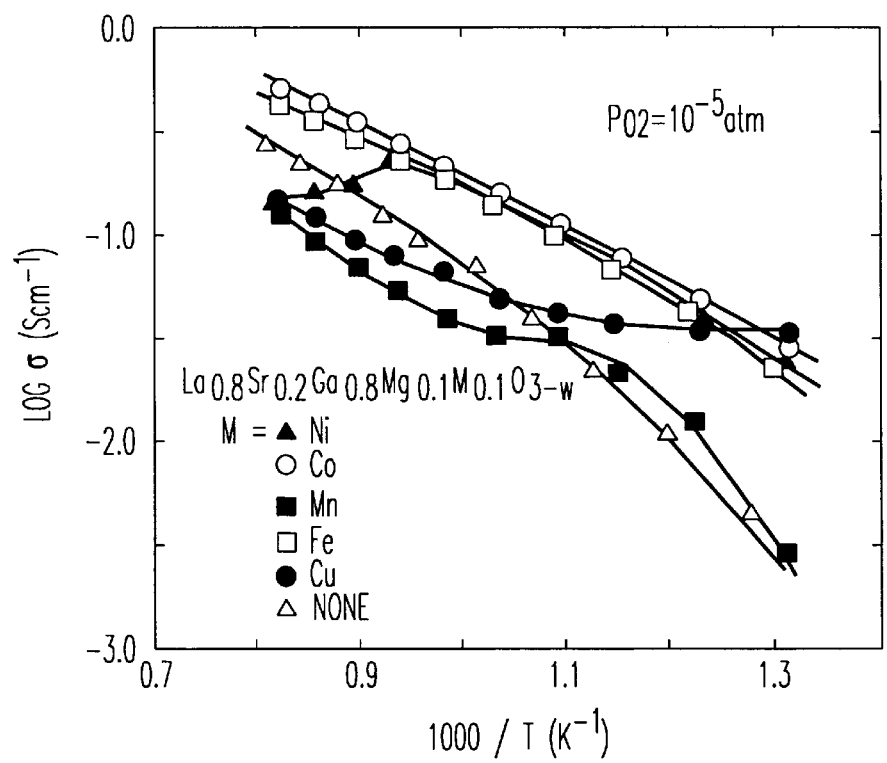
FIG. 2 is a graph showing electrical conductivity of a 5-element compound oxide obtained by substituting transition metals for part of the Mg of the 4-element perovskite oxide-ion conductor of FIG. 4, in comparison with the conductivity shown by the 4-element perovskite compound oxide.

FIG. 2 shows, by way of example, the electrical conductivity of a 5-element oxide-ion conductor (Ln is La, A is Sr, B1 is Mg and B2 is M) obtained by substituting part of the Mg in the reference 4-element compound oxide $La_{0.8}Sr_{0.2}Ga_{0.8}Mg_{0.2}O_{3-w}$ with a transition metal (represented by "M" in the formula of FIG. 2).

As will be understood from this Figure, the 5-element compound oxide thus obtained exhibits a much higher electrical conductivity than the reference 4-element compound oxide, provided that the B2 atom (M in the general formula of FIG. 2) is Co or Fe. In particular, the reference 4-element compound oxide exhibits a drastic reduction in the conductivity at low temperatures, i.e., in the range of about 630° C. or below, 1.1 or greater in terms of the abscissa value. At the low temperature range, therefore, the contribution of Co or Fe to the improvement in the conductivity is more remarkable. When the B2 atom (M) is Ni, the conductivity of the 5-element compound oxide exceeds that of the reference 4-element compound oxide, when the temperature is about 840° C. or less (0.9 or greater in terms of the abscissa value).

When the B2 atom (M) is Cu, the conductivity of the 5-element compound oxide exceeds that of the reference 4-element compound oxide, when the temperature is about 630° C. or less (1.1 or greater in terms of the abscissa value). It is to be noted that, even when the temperature is lowered below the above-mentioned thresholds, the conductivity is not further reduced but remains substantially constant. Consequently, the highest conductivity is obtained when the abscissa value is 1.3 or above, i.e., about 500° C. or less.

Therefore, when the B2 atom is Ni or Cu, the 5-element compound oxide is preferably used as an oxide-ion conductor at comparatively low temperatures. It is to be understood, however, that the reference 4-element compound oxide ($La_{0.8}Sr_{0.2}Ga_{0.8}Mg_{0.2}O_{3-w}$) exhibits a very high conductivity in comparison with stabilized zirconia, even at high temperatures above 1.0 in terms of the abscissa value. It is therefore understood that the 5-element compound oxide in which B2 atom is Ni or Cu exhibits sufficiently high conductivity as compared to the stabilized zirconia, not only at low temperatures but also at high temperatures.

When Mn is used as the transition metal for the B2 atoms, the conductivity is lower than that of the reference 4-element compound oxide at high temperatures of 1.1 or less in terms of the abscissa value. In this case, the conductivity is almost the same as that of the reference 4-element compound oxide even at low temperatures of 1.1 or greater in terms of the abscissa value. Thus, substitution of part of the Mg with this transition metal does not provide any substantial improvement in conductivity regardless of the temperature. The transition metal for the B2 atoms, therefore, is one, two or more elements selected from the group consisting of Co, Fe, Ni and Cu that provides, for at least part of the temperature range, improvement in the conductivity over the reference 4-element compound oxide.

The 5/4-element compound oxides of the invention exhibits reduced electrical conductivity or ion transference number, when the atomic ratio of the doping atoms, i.e., the atomic ratio "x" of the A atoms at the A site or the total atomic ratio "x+y" of the B1 and B2 atoms at the B site, fails to fall within the range stated above.

Figure 3:
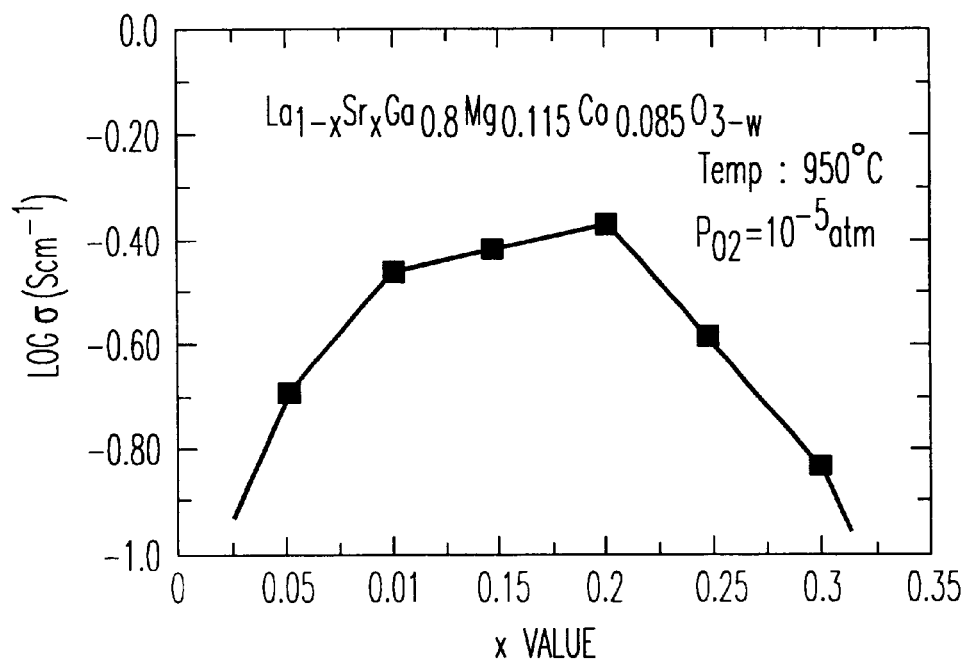
FIG. 3 is a graph showing the relationship between electrical conductivity and the atomic ratio "x" of A atoms as the A-site dopant in an oxide-ion conductor of a 5-element compound oxide in accordance with the present invention.

FIG. 3 shows the change in the conductivity in relation to a change in the ratio of the A atoms (Sr). It will be seen that the conductivity is lowered when the atomic ratio "x" does not fall within the range from 0.05 to 0.3, i.e., when the atomic ratio of the Ln atoms do not fall within the range from 0.7 to 0.95.

Figure 4A:
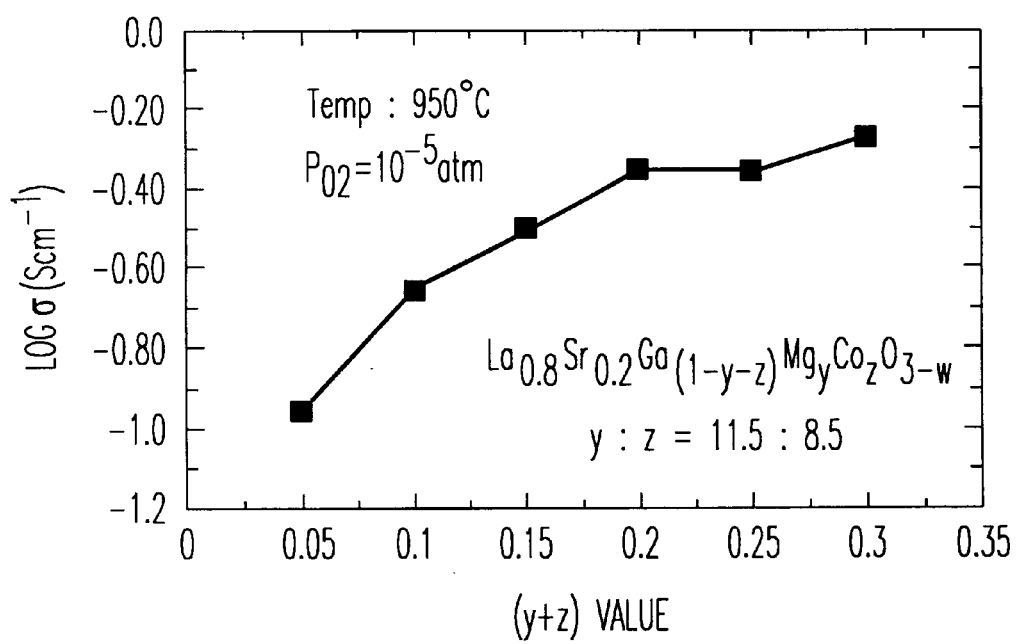
FIG. 4A is a graph showing the relationship between electrical conductivity and the total atomic ratio (y+z) (y:z=11.5:8.5) of B1 and B2 atoms as the B-site dopants in a oxide-ion conductor of a 5-element compound oxide in accordance with the present invention.

FIG. 4A shows the change in the conductivity as observed when the total atomic ratio "y+z" of the B1 atoms and B2 atoms is changed while the ratio y: z is fixed at 11.5: 8.5. The conductivity increases as this total atomic ratio "y+z" increases. However, an increase in the value "y+z" causes a reduction in the ion transference number, as will be seen from FIG. 4B. More specifically, the ion transport number is reduced down below 0.7 when the value "y+z" exceeds 0.3, i.e., when the atomic ratio of Ga falls below 0.7.

Figure 5:
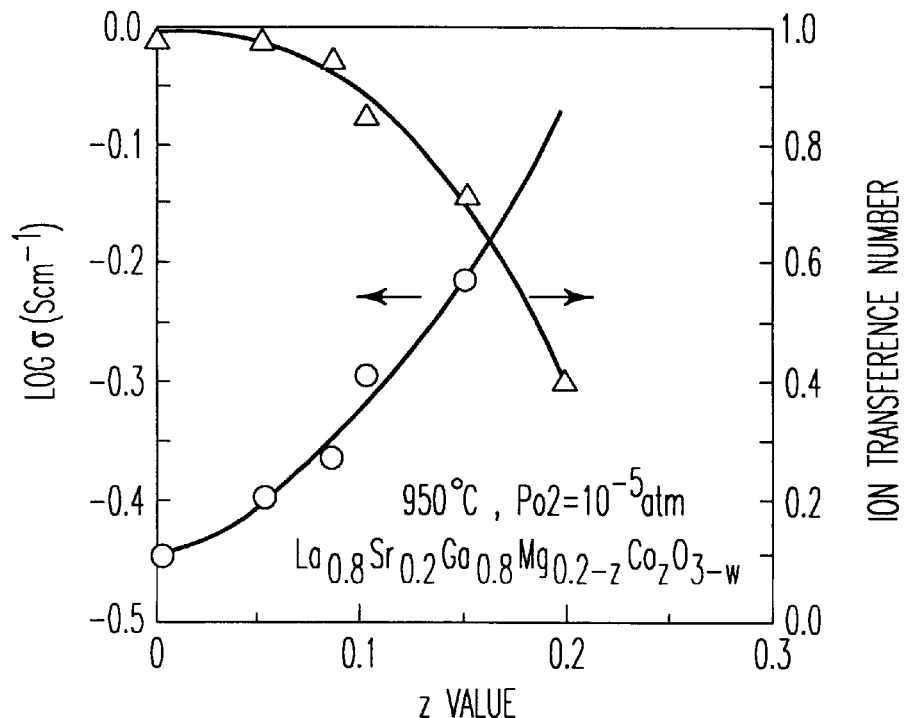
FIG. 5 is a graph showing the dependences of the electrical conductivity and the ion transference number on the atomic ratio "z" of B2 atoms as the transition metal atom that is part of the dopant of the B site of oxide-ion conductor of a 5/4-element compound oxide in accordance with the present invention.

Referring now to FIG. 5, as to the B2 atom which is one of the two dopant atoms of the B site, the conductivity increases when the "z" value that indicates the atomic ratio of the B2 atoms (Co) increases. This is because the transition metal, as the B2 atoms, tends to develop n- or p-type electron-based conduction as a result of variation in valency. Consequently, the proportion of the oxide-ion conductivity, i.e., the ion transference number, decreases correspondingly.

As will be seen from FIG. 5, a 5-element compound oxide having a "z" value not greater than 0.15 provides an ion transference number of 0.7 or greater. In particular, an ion transference number as high as 0.9 or higher is obtained when the "z" value is 0.10 or less. Consequently, the 5-element compound oxide with such a value of "z" functions as the aforesaid oxide-ion conductor in the narrower sense. In this case, however, the B site must contain to some extent non-transition metal atoms as the B1 atoms in the B site, in order to keep the proportion of the electron-based conduction to 0.3 or less. As will be described later, this material can suitably be used as the material of an electrolyte of a solid oxide fuel cell, a gas sensor, an oxygen separator membrane of an electrochemical oxygen pump, and so forth.

Conversely, a "z" value exceeding 0.15 serves to reduce the ion transference number to a level below 0.7, so that the compound oxide functions as an electron-ion mixed conductor. As stated before, such an electron-ion mixed conductor also falls within the scope of the oxide-ion conductor of the present invention. It is to be noted that the ion transference number is still as high as 0.3, even when the "z" value is 0.2 ("y" value is 0), i.e., even in a 4-element compound oxide in which Mg as the B1 atom has been completely replaced with Co (B2 atoms). Such a 4-element compound oxide therefore can satisfactorily function as the electron-ion mixed conductor and, hence, serves as the oxide-ion conductor of the present invention, while exhibiting the greatest conductivity, as mentioned before. As will be explained later, such a mixed conductor can advantageously be used as the material of an air electrode of a solid oxide fuel cell, or a gas separator membrane.

The following conditions are preferably met in the general formula (1):
Ln is La, Nd or a mixture of La and Nd, more preferably La
A is Sr
B1 is Mg
B2 is Co
x=0.10 to 0.25, more preferably 0.17 to 0.22
y=0 to 0.17, more preferably 0.09 to 0.13
y+z=0.10 to 0.25, more preferably 0.15 to 0.20
The "z" value is as follows:

In order that the conductor of the invention functions as an oxide-ion conductor in the narrower sense, having a high oxide-ion conductivity (0.7 or higher, preferably 0.9 or higher in terms of the ion transference number), it is desired that the "z" value falls within the range of 0.02 to 0.15, more preferably 0.07 to 0.10. Conversely, when it is desired that the conductor of the invention serves as an electron-ion mixed conductor, the "z" value preferably meets the condition of $0.15 < z \leq 0.3$, more preferably $0.15 < z \leq 0.25$.

In a preferred form of the present invention, the conditions are: Ln La, A=Sr, B=Mg, B2=Fe, x=0.1 to 0.3, y=0.025 to 0.29, z=0.01 to 0.15, and y+z=0.035 to 0.3. Thus, the preferred form of the oxide-ion conductor has the formula (2):

$$La_{1-x}Sr_xGa_{1-y-z}Mg_yFe_zO_{3-w} \quad (2)$$

wherein,
x is 0.1 to 0.3;
y is 0.025 to 0.29;
z is 0.01 to 0.15; and
y+z is 0.035 to 0.3.

The oxide-ion conductor of formula (2) exhibits a high conductivity, without showing any dependency on oxygen partial pressure. Although a p-type semiconduction makes a slight contribution to the electrical conductivity under high oxygen partial pressures, the oxide-ion conductivity is predominant over a wide range of oxygen partial pressures from 1 to $10^{-21}$ atm (i.e., from reducing atmosphere to oxidizing atmosphere). In addition, the ion transference number of the electrical conductivity is as high as 0.9 or greater. Considering the high ion transference number exhibited regardless of the oxygen partial pressure, as well as the high electrical conductivity, it is understood that the improvement in the electrical conductivity achieved by the oxide-ion conductor of the present invention mainly owes to the improvement in the oxide-ion conductivity.

Figure 6:
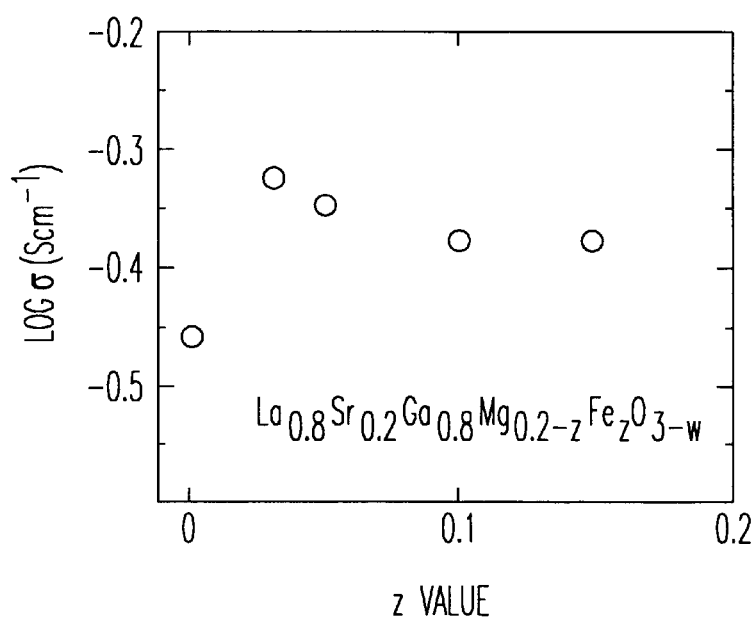
FIG. 6 is a graph showing the electrical conductivity (950° C., oxygen partial pressure of $10^{-5}$ atm) of a compound oxide expressed by $La_{0.8}Sr_{0.2}Ga_{0.8}Mg_{0.2-z}Fe_zO_{3-w}$ as an embodiment of the oxide-ion conductor of the present invention for a varying value "z".

FIG. 6 shows the electrical conductivity at 950° C. exhibited under oxygen partial pressure of $10^{-5}$ atm by a 5-element compound oxide ($La_{0.8}Sr_{0.2}Ga_{0.8}Mg_{0.2-z}Fe_zO_{3-w}$) obtained by substituting Fe for part of the Mg of the reference 4-element compound oxide expressed by $La_{0.8}Sr_{0.2}Ga_{0.8}Mg_{0.2}O_{3-w}$. As will be understood from this Figure, the 5-element compound oxide obtained by substituting part of the Mg with Fe exhibits higher electrical conductivity than the reference 4-element compound oxide in which the value "z" is zero. In particular, electrical conductivity is high when the value "z" ranges from 0.01 to 0.05, and is maximized when the value "z" is around 0.03.

Figure 7A:
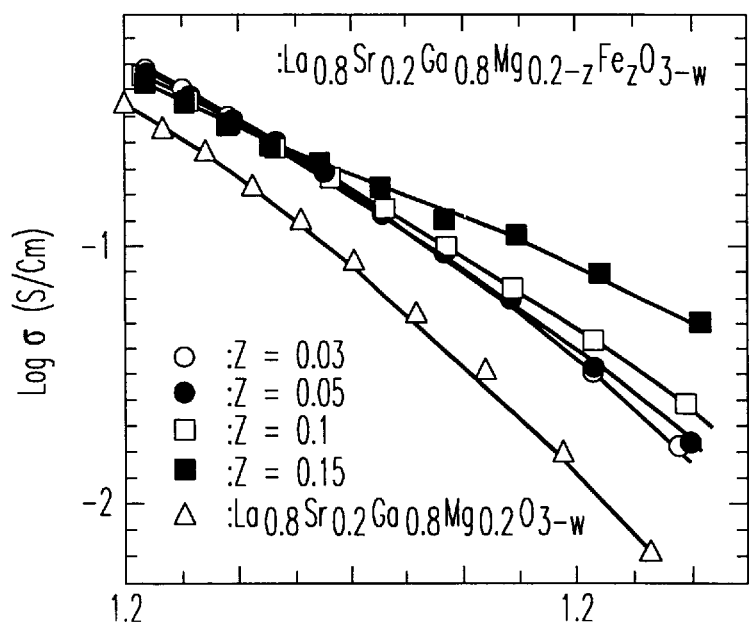
FIG. 7A shows the dependence on temperature of the oxide-ion conductor of the invention expressed by $La_{0.8}Sr_{0.2}Ga_{0.8}Mg_{0.2-z}Fe_zO_{3-w}$ at an oxygen partial pressure of $10^{-5}$ atm.
Figure 7B:
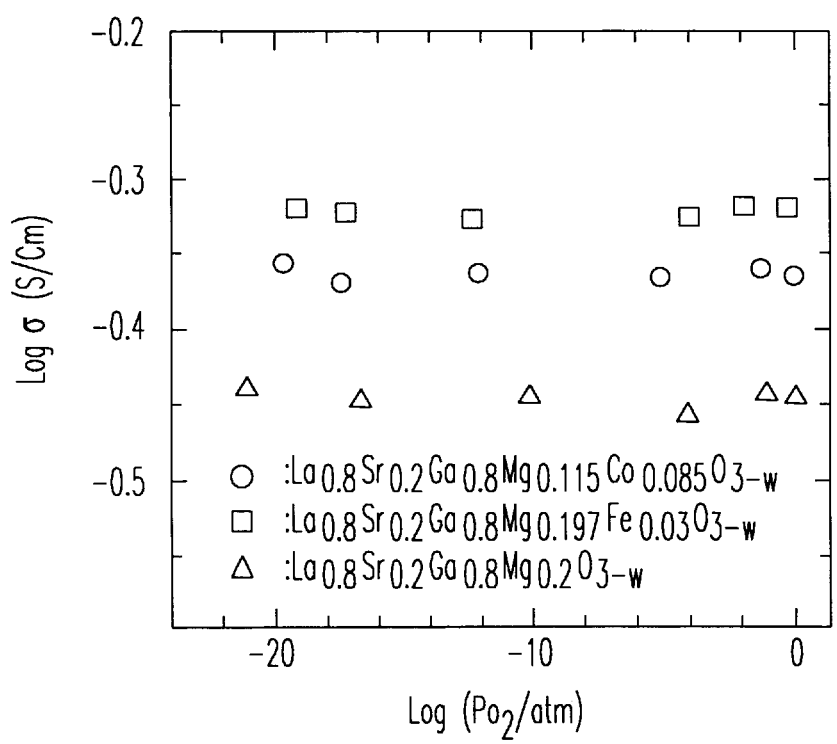
FIG. 7B shows the dependence on oxygen partial pressure of the oxide-ion conductor of the invention expressed by $La_{0.8}Sr_{0.2}Ga_{0.8}Mg_{0.2-z}Fe_zO_{3-w}$ at temperature of 950° C.

FIG. 7A shows changes of electrical conductivity with temperature (Arrhenius plot) exhibited by the 5-element compound oxide $La_{0.8}Sr_{0.2}Ga_{0.8}Mg_{0.2-z}Fe_zO_{3-w}$, (z=0.03, 0.05, 0.1 and 0.15) of the general formula (2) in comparison with that shown by the 4-element compound oxide in which the value "z" is zero, while FIG. 7B shows dependency on oxygen partial pressure of electrical conductivity exhibited by the 5-element compound oxide of the general formula (2) with the "z" value fixed to 0.03, as well as by other related compounds.

As will be seen from these figures, the 5-element compound oxide shows a high electrical conductivity over a wide ranges of temperature and oxygen partial pressure, and exhibits almost no dependency of electrical conductivity on the oxygen partial pressure. It is therefore understood that this 5-element compound oxide exhibits ion transference number as high as 0.9 or above.

This 5-element compound oxide can suitably be used as the material of an electrolyte of a solid oxide fuel cell, a gas sensor, an oxygen separator membrane of an electrochemical oxygen pump, and so on. It will be understood that this material will provide products superior to those relying on stabilized zirconia, because electrical conductivity exhibited by this material is higher than that of stabilized zirconia and exhibits only small change in response to changes in temperature and oxygen partial pressure.

Among the compositions expressed by the general formula (2), the compositions that meet the following conditions are particularly preferred:
x=0.15 to 0.25, in particular 0.17 to 0.22
y=0.09 to 0.24, in particular 0.10 to 0.20
z=0.01 to 0.05, in particular about 0.03
y+z=0.10 to 0.25, in particular 0.15 to 0.22.

The oxide-ion conductor of the present invention can be obtained by preparing powders of oxides of the constituent elements, mixing the powders at a predetermined ratio, forming the mixture into a predetermined form by suitable means, and sintering by heating the formed mixture. The materials of the powder need not always be the oxides: namely, precursors such as carbonate, carboxylate, nitrates and so forth, that form oxides through thermal decomposition or oxidation during heating, can be used equally well. The heating temperature for sintering is generally 1200° C. or higher, more preferably 1300° C. or higher. The heating time period ranges from several hours to several tens of hours. In order to shorten the heating time period, the raw material mixture may be pre-heated at a temperature lower than the heating temperature. The pre-heating can be accomplished by, for example, heating the raw material mixture for 1 to 10 hours at a temperature between 500 and 1300° C. The pre-heated mixture is crushed as required and is then formed and finally heated. The forming may be conducted by using a suitable known technique, such as uniaxial compressing, isostatic pressing, extruding and tape casting. The heating, as well as the pre-heating, is preferably conducted in an oxidizing atmosphere such as air or in an inert gas atmosphere.

Among the oxide conductors of the present invention, the 5-element compound oxides having a "y" value of 0.025 or greater and a "z" value of 0.15 or less unction as an oxide-ion conductor in the narrower sense, since the oxide-ion conductivity is the dominant part of the electrical conductivity (0.7 or greater in terms of the ion transference number). This type of material, therefore, can be used for various oxide-ion conductors, in place of stabilized zirconia which has been conventionally used, e.g., as the material of an electrolyte of a solid oxide fulel cell, gas sensor, and so forth. This type of oxide-ion conductor of the present invention exhibits higher oxide-ion conductivity than the stabilized zirconia and can function even at low temperatures and, hence, is expected to provide products superior to those produced from stabilized zirconia.

Oxide-ion conductors such as YSZ are finding a variety of uses. One of the important uses is as the material of the electrolyte of a solid oxide fuel cell (SOFC). The most up-to-date SOFC has a cell structure having an electrolyte composed of a thin film of $Y_2O_3$ stabilized zirconia (YSZ), an air electrode (cathode) formed of a material having a perovskite structure exhibiting electron-based conductivity such as Sr-doped $LaMnO_3$, and a fuel electrode (anode) constituted by a metal such as Ni or a cermet such as Ni-YSZ. The SOFCs using YSZ as the electrolytes are usually designed to operate at high temperatures around 1000° C., because the conductivity of YSZ is low at low temperatures and because a high power generating efficiency is obtained by virtue of co-generation which employs power generation by a turbine generator using the heat of the exhaust gas from the SOFC.

In general, SOFC exhibits a large voltage drop due to resistance of the electrolyte. Thus, the thinner the electrolyte, the greater the output power. For this reason, the YSZ constituting the electrolyte is used in the form of film having a thickness as small as 30 to 50 $\mu$m. The oxide-ion conductivity of YSZ, however, is still too small. In order to provide a practical and satisfactory performance, therefore, it is necessary that the SOFC is heated to a temperature of about 1000° C. It has been reported that a practical output density of 0.35 $W/cm^2$ or so can be attained at operating temperatures around 1000° C. when a thin-film YSZ of 30 $\mu$m thick is used. In order to achieve a higher output power or to reduce the operating temperature, reports have been made on the results of experiments conducted by using YSZ films of several $\mu$m to 10 $\mu$m. Such extremely thin YSZ films, however, are not preferred from the viewpoint of reliability, because the gas impermeability, which is an essential requirement for the film, is not ensured with such extremely thin films.

The oxide-ion conductor in the narrower sense of the invention, constituted by the 5-element perovskite oxide, can provide much higher oxide-ion conductivity than YSZ and, hence, can provide greater output power than that provided by the YSZ film, even when the electrolyte film of this material has a thickness of 0.5 mm (500 $\mu$m) which is obtainable with sintering techniques With such an electrolyte film, the maximum output power density, although it varies depending on the kind of the B2 atoms or the atomic ratios, exceeds that offered by the SOFC using the YSZ thin film of 30 $\mu$m thick, even at temperatures around 1000° C. At a lowered operating temperature of 800° C., the maximum output power density is several times, e.g., three times or more, greater than that obtained with the use of the thin YSZ film. Alternatively, an electrolyte film formed of this 5-element perovskite oxide, even when the thickness is as large as about 200 $\mu$m, provides an output power density equivalent to that provided at 1000° C. by the conventional YSZ film of 30 $\mu$m thick, even at a lower temperature from 600 to 700° C.

When the oxide-ion conductor of the present invention is used as the electrolyte of a solid oxide fuel cell (SOFC), the specific composition can suitably be selected in accordance with the operating temperature of the SOFC. For instance, when co-generation is performed employing power generation by a turbine generator using exhaust gas, it is necessary that the operating temperature is as high as around 1000° C. For such uses, the electrolyte is preferably formed of a 5-element compound oxide in which Co or Fe, in particular Co, is used as the B2 atoms, because such an oxide exhibits high oxide-ion conductivity at high temperatures. However, if the operating temperature is lower, e.g., 800° C. or so, a 5-element compound oxide employing Ni as the B2 atoms can also be used. A 5-element compound oxide employing Cu as the B2 atoms also can be used when the operating temperature is as low as 600° C. or below.

The power generating efficiency of an SOFC is not significantly lowered even when the operating temperature is as low as 600 to 700° C., provided that power generation using steam or exhaust gas is used for power generation or otherwise emitted heat is used effectively as a source of thermal energy. Such a lowered operating temperature permits the use of an iron-based material such as stainless steel as a structural material of SOFC. The use of such an iron-based material remarkably reduces the material cost as compared with the case where the operating temperature as high as 1000° C. or so requires the use of expensive Ni-Cr alloys or ceramics. It has been impossible to produce an SOFC operable at such low temperatures using YSZ. In accordance with the present invention, however, it is possible to make a variety of classes of SOFC coping with a variety of demands or environments of use, including SOFCs operable at comparatively low temperatures and SOFCs operable at comparatively high temperatures.

In particular, the oxide-ion conductor composed of the 5-element compound oxide expressed by the general formula (2) provides an electrolyte of SOFC that can satisfactorily function at any temperature within a wide temperature range, from comparatively low temperatures of 600–700° C. to high operating temperature of 1000° C. or so. Therefore, when this type of oxide-ion conductor is selected as the material of the electrolyte, a variety of classes of SOFCs adapting to a wide range of operating temperatures can be obtained without requiring selection of other types of conductor as the material of the electrolyte.

As discussed before, the 5-element compound oxide of the present invention exhibits a very high oxide-ion conductivity as compared with YSZ. The electrolyte film made of this material, therefore, can have a large thickness, e.g., 0.5 mm or so, that can be obtainable with sintering techniques. Consequently, mechanical strength, as well durability, is remarkably improved. In addition, the SOFC incorporating such an electrolyte can provide a greater maximum output power density than SOFCs that employ YSZ electrolyte films.

There is no restriction on the type of the electrodes of an SOFC that uses an electrolyte made from the 5-element oxide of the present invention. For instance, the air electrode may be formed from $SM_{0.5-0.7}Sr_{0.5-0.3}CoO_{3-w}$, while the fuel electrode may be form of Ni as a metal. This cell structure provides increased power, particularly at low temperatures. For instance, a high output power density of 1.5 W/cm$^2$ is obtained even at a comparatively low temperature of 800° C. The output power density is still high enough to meet the practical demand even at a further lowered temperature of 600° C. It is therefore expected that a solid oxide fuel cell capable of operating at low temperatures of 600° C. or below, that can not be obtained with the known arts, is attainable by the present invention. In order to reduce electrode overvoltage, the fuel electrode may be constituted by a cermet such as Ni—CeO$_2$. At the present state of technology, YSZ has its greatest use in oxygen sensors which now find a big use in the control of the air-fuel ratio of automotive engines, control of various industrial processes, and so forth. This type of oxygen sensor is referred to as a "solid electrolyte oxygen sensor", and measures oxygen concentrations based on the principle of an oxygen concentration cell. When a difference in oxygen partial pressure develops across an oxide-ion conductor, an electromotive force appears as a result of diffusion of oxide ions into the material to form an oxygen concentration cell. It is therefore possible to measure the oxygen partial pressure by sensing the electromotive force between electrodes provided on both sides of the oxide-ion conductor. The solid electrolyte oxygen sensor can be employed not only in the measurement of oxygen gas but also for sensing other gases containing oxygen, such as $SO_x$, $NO_x$, and so forth.

The oxygen sensor made of YSZ is comparatively inexpensive but undesirably exhibits a reduction in conductivity at low temperatures. Thus, this type of oxygen sensor can be used only at comparatively high temperatures not less than 600° C. Thus, the solid electrolyte oxygen sensor has only limited use. In contrast, the 5-element oxide-ion conductor proposed by the present invention (inclusive of those meeting the conditions of $y \geq 0.025$ and $z \leq 0.15$ in the formula (1), as well as those expressed by the general formula (2)), in which the oxide-ion conductivity is predominant, exhibits higher oxide-ion conductivity than YSZ and, therefore, can suitably be used as the materials of gas sensors, in particularly oxygen sensors. The gas sensors using this material can satisfactorily be used even at low temperatures of 600° C. or below.

The 5-element oxide-ion conductor proposed by the invention (inclusive of those meeting the conditions of $y \geq 0.025$ and $z \leq 0.15$ in the formula (1), as well as those expressed by the general formula (2)), in which the oxide-ion conductivity is predominant, can also be used as an oxygen separator membrane of an electrochemical oxygen pump. When an electric potential difference is given across a separator membrane made of an oxide-ion conductor, electrical current flows across the membrane due to movement of oxide ions, so that oxygen moves uni-directionally from one to the other side of the membrane. This is the principle of an oxygen pump. For instance, when air is supplied to one side of the membrane, air enriched with oxygen is obtained at the other side of the membrane. Thus, the membrane is used as an oxygen separator.

The oxygen separator membranes are used in, for examples, military aircraft and helicopters, for the purpose of generating oxygen-enriched air from the ambient air having a low oxygen concentration, and is expected to be usable also as an oxygen source in place of oxygen cylinders for medical purposes.

The 5/4-element perovskite oxide ion conductors ($z > 0.15$) of the present invention, that exhibits electron-ion-mixed conductivity, i.e., ion transference number of 0.70 or less, can function as an ionizing catalyst that imparts electrons to oxygen. This material exhibits both high electron-based conductivity necessary to enable the material to function as an electricity collector and high oxide-ion conductivity required to enable the material to function as an oxide-ion conductor for injecting oxide ions into an electrolyte. This material therefore can suitably be used as the material of an air electrode of an SOFC described before. It is preferred that at least part of air electrode is made of this material.

In particular, when the electrolyte of an SOFC is formed of a 5-element oxide-ion conductor in the narrower sensor, of the invention (inclusive of those meeting the conditions of $y \geq 0.025$ and $z \leq 0.15$ especially $z \leq 0.10$ in the formula (1), as well as those expressed by the general (2)) in which the oxide-ion conductivity is predominant, it is preferred that the air electrode of the SOFC is made of one of the 5/4-element materials of the invention exhibiting electron-ion-mixed conductivity (inclusive of those meeting the condition of $z > 0.15$ in the formula (1) and the value "y" may be zero), because such a combination of the electrolyte and the air electrode serves to improve the performance of the SOFC by virtue of the fact that both the electrolyte and the air electrode of the SOFC are made of similar materials.

To explain in more detail in this connection, conventional SOFCs employ different materials as the constituents of the electrolyte and air electrode. For instance, a known SOFC employs an electrolyte made of YSZ and an air electrode constituted by $La(Sr)CoO_3$. At the microscopic scale of the atomic level a very thin interface layer in which the materials of the electrolyte and the air electrode co-exist is formed therebetween, and thus the resulting interfacial resistance causes a voltage drop, reducing the output power. When both the electrolyte and the air electrode are made of similar materials, generation of the interlayer is suppressed so as to reduce the resistance which would cause the output reduction.

Use of different types of materials for the electrolyte and the air electrode poses another problem; namely, an increase in the thermal stress due to difference in the thermal expansion coefficient during heating and/or cooling. Such thermal stress can also be reduced when the same type of materials is used for the electrolyte and the air electrode.

The resistance across the interface layer, as well as the thermal stress, can be further reduced when one, two or more interlayers having compositions intermediate between those of the electrolyte and the air electrode are provided therebetween so that the composition progressively and substantially changes continuously from that of the electrolyte to that of the air electrode.

As stated above, the fuel electrode may be made of various kinds of material that have been conventionally used. However, in accordance with the present invention, the fuel electrode is preferably made of a material composed of (1) Ni and (2) a compound expressed by the formula $Ce_{1-m}C_mO_{2-w}$ (C being one, two or more elements selected from the group consisting of Sm, Gd, Y and Ca, "m" being from 0.05 to 0.4, and w corresponds to the number of oxide holes), which may also be referred to as $Ce_{1-m}C_m$ oxide. The ratio (1):(2) between Ni and the compound preferably ranges from 95:5 to 20:80 in terms of volumetric ratio. More preferably, the value "m" is from 0.1 to 0.3, and the volumetric ratio (1):(2) ranges between 90:10 and 40:60.

No specific restriction is posed in regard to the structure of the SOFC. The SOFC may be cylindrical or planar. A planar SOFC may have a stack-type or monolithic structure. In any case, the basic cell structure has three layers composed of an air electrode, a fuel electrode and an electrolyte sandwiched therebetween. Thus, the electrolyte is held in contact with the air electrode on one side and with the fuel electrode on the other side. The electrolyte layer must be impermeable to gases, while the air electrode and the fuel electrode are porous and, hence, gas-permeable. In the case of a cylindric SOFC, a fuel gas, e.g., hydrogen, and air (or oxygen) are separately supplied to the interior and the exterior of a multiplicity of cylindrical cells that are connected together through interconnectors provided on the outer surfaces thereof. In the case of a planar SOFC, the fuel gas and the air are supplied by means of generally planar inter-connectors which provide passages through which the fuel gas and the air are supplied separately. A stacked SOFC can be formed by alternately stacking the three-layered basic cell structures and the planar inter-connectors.

One of the reactions that controls the rate of the electrode reaction in a SOFC is the ionization of oxygen that occurs on the air electrode which is expressed by the following formula:

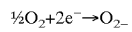

This reaction takes place at the three-phase boundary of the air, the air electrode and the electrolyte. A greater area of the three-phase boundary provides a correspondingly greater magnitude of the reaction. For this reason, therefore, it has been attempted to employ a corrugated three-layered basic cell structure in place of the planar three-layered basic cell structure.

In a preferred form of the present invention, a cell configuration is employed in which, as shown in FIG. 8, convex and concave regions are formed on both surfaces of the electrolyte, and particles of the material of the air electrode and the fuel electrode are deposited on the convex and concave surfaces of the electrode. In such a cell structure, the convex and concave surface portions of the electrolyte may be porous, although the core part of the electrolyte must be impermeable to gases. Preferably, the convex and concave surface portions are made of a material that exhibits electron-ion-mixed conductivity, although this surface portion may be made of the same material as the electrolyte, i.e., an oxide-ion conductor in the narrower sense. For instance, the convex and concave surface portions contacting the air electrode may be constituted by a material of the invention that exhibits electron-ion-mixed conductivity (z>0.15). In such a case, the individual particles deposited on the convex and concave surface portions are preferably made of a material in which the electron-based conductivity is dominant, e.g., a conventional air electrode material.

The described structure of the SOFC can be obtained through a process that has the steps of: attaching particles of the ion-electron-mixed conductor material on the surfaces of the electrolyte by heating, depositing finer particles of an electron-based conductor material on the surfaces carrying the attached particles, and heating the surfaces. Alternatively, a similar structure can be implemented simply by depositing a mixture of the particles of the ion-electron-mixed conductor material and the particles of the electron-based conductor material at a predetermined mixing ratios, followed by heating.

Figures 9A, 9B:
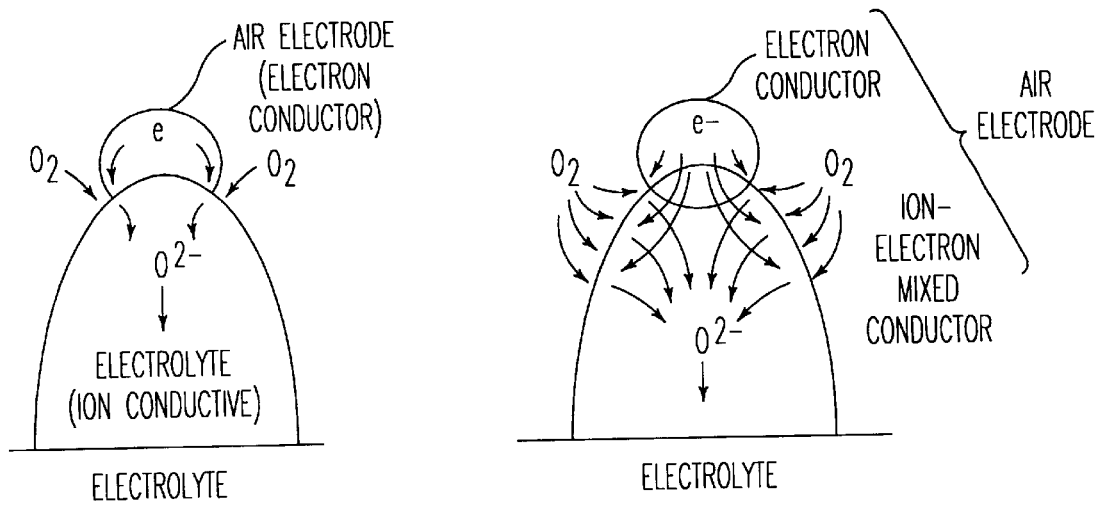

Conventionally, electron-based conductor materials in which conductivity by electrons is predominant, having a low ion transference number, such as $La(Sr)CoO_3$, $La(Sr)MnO_3$ or the like, have been used as the materials for air electrodes. With this type of material, it is impossible to inject oxide ions into the electrolyte through the material of the air electrode, although oxygen in the air can satisfactorily be ionized into oxide ions. Therefore, in a conventional SOFC, the convex and concave surface portion of the electrolyte adjacent to the air electrode as shown in FIG. 8 are formed from the electrolyte material, and the air electrode material is deposited in the form of particles on these convex and concave surface portions. In such a case, ionization of the oxygen takes place only at the interface of the three phases of the electrolyte layer, the air electrode particle and the air, i.e., only unidimensionally at the circumference at which the ultra-fine particle of air electrode contacts the electrolyte layer as shown in FIG. 9A. Consequently, polarization of the air electrode is enhanced to reduce the output power of the SOFC. In addition, the electrolyte layer must be held in contact with the air, in order to catch the oxide ions, and therefore the air electrode does not completely cover the electrolyte layer. Consequently, the amount of deposition of particles is limited. This renders unstable the electrical connection to an external terminal that relies upon the electron-based conductivity of the air electrode. Alternatively, in order to obtain a sufficiently stable electrical connection, a bridging structure of a conductive material rich in voids or paths for the air, is required so as to bridge the particles of the air electrode material. In such a case, however, the voids may impede the passage of the gases.

In contrast, the air electrode material in accordance with the present invention exhibits ion-electron mixed conductivity and, hence, can ionize by itself the oxygen in the air into oxide ions. It is therefore possible to use a structure in which the convex and concave surface portions of the air electrode side (see FIG. 8) are formed from this air-electrode material that exhibits ion-electron-mixed conductivity and the depositing particles are formed from a conventional air electrode material. In such a structure, the ionization of oxygen takes place, as shown in FIG. 9B, at the interface between two phases: the convex and concave surface portions of the mixed conductor material and the air, i.e., at the two-dimensional area presented by the entire external surface of this material. Consequently, ionization efficiency is remarkably increased and polarization of the air electrode is prevented, thus enhancing the output power of the SOFC. The oxide ions generated as a result of the ionization are made to flow into the electrolyte through the air electrode material, by virtue of the oxide-ion conductivity provided by the mixed-conductive air electrode material. The mixed-conductive air electrode material constituting the convex and concave surface is also capable of performing conduction by means of electrons and, therefore, can supply an electrical current to the external electrode. To assist this action, particles of electron-based conductor material are deposited on the convex and concave surface portion of the electrolyte adjacent to the air electrode.

As explained before, the fuel electrode is preferably made of a material composed of Ni and a ceria-type material ($Ce_{1-m}C_mO_{2-w}$). In this case also, the ceria-type material that is an oxide-ion-mixed conductor constitutes the concave and convex surface portions of the electrolyte of the fuel electrode side, and the particles deposited thereon are made of Ni, an electron-based conductor. With this arrangement, delivery of oxide ions to $H_2$ is performed in the two-dimensional region as in the case of the air electrode, so that the efficiency of the $H_2O$ formation reaction is greatly improved.

The oxide-ion conductor (z>0.15) of the present invention, exhibiting electron-ion-mixed conductivity, can also be used as a gas separator membrane that separate gases by making use of differences in gas concentrations. The gas separator membrane does not need an external supply of electrical potential difference across the membrane. Namely, the actuating power for the separation is derived from the difference in oxygen concentration between the gases on both sides of the membrane. When such an oxygen concentration differential exists, oxide ions move from the gas having the higher oxygen concentration to the gas having the lower oxygen concentration. Electrons are made to move in the opposite direction so as to compensate for the movement of the oxide ions. Thus, the material is required to have a certain degree of electron-based conductivity, as well as oxide-ion conductivity, in order to function. In other words, the material constituting the gas separator membrane has to be an electron-ion-mixed conductor.

This gas separator membrane can be used not only for the separation of oxygen but also for other purposes such as, for example, decomposition of water and $NO_x$. In the case of water, when decomposition into oxide ions and hydrogen takes place on the membrane, a difference in oxide ion concentration is developed across the membrane. This difference in oxide-ion concentration then serves as the activating power to create a flow of oxide ions, while hydrogen is left on the surface of the membrane. It is thus possible to generate hydrogen from water. Similarly, $NO_x$ is made harmless by being decomposed into nitrogen and oxygen by means of the gas separator membrane.

The oxide-ion conductor in accordance with the present invention has further extensive use such as electrochemical reactors, oxygen-isotope separator membranes, and so on.

Having generally described this invention, a further understanding can be obtained by reference to certain specific examples which are provided herein for purposes of illustration only and are not intended to be limiting unless otherwise specified.

EXAMPLES

Example 1

Powders were prepared from $La_2O_3$, $SrCO_3$, $Ga_2O_3$, $MgO$ and one or more transition metal oxides selected from $CoO$, $Fe_2O_3$, $Ni_2O_3$, $CuO$ and $MnO_2$. These powders were mixed to provide a composition expressed by $La_{0.8}Sr_{0.2}Ga_{0.8}Mg_{0.1}M_{0.1}O_{3-w}$ ("M" being a transition metal). After sufficient blending, the mixture was pre-heated at 1000° C. for 6 hours. The pre-heated mixture was then crushed and compression-formed into disks 0.5 mm thick and 15 mm diameter, by means of a isostatic press, and the disks thus formed were sintered by being heated at 1500° C. for 6 hours. The crystal structures of the sintered disks were examined by means of X-ray diffraction and confirmed to have the perovskite structure.

Electrical conductivity of the sintered body was examined as follows. Rectangular parallelepiped test pieces were cut out from the disk-shaped sintered bodies. After application of a platinum paste as electrodes, platinum wires were connected to each test piece, followed by heating at temperatures varied within the range of from 950 to 1200° C. for a time period of 10 to 60 minutes. Then, each test piece was tested in equipment capable of providing any desired oxygen partial pressure and temperature, through measurement of electrical resistance in accordance with a DC 4-terminal or AC 2-terminal measuring method. The oxygen partial pressure was varied by using mixture gases of $O_2$—$N_2$, $CO$—$CO_2$ and $H_2$—$H_2O$.

The results of the measurements are shown in FIGS. 2 and 10. More specifically, FIG. 2 shows the electrical conductivity (Arrhenius plot of conductivity) as observed at varying temperature under a fixed oxygen partial pressure of $10_{-5}$ atm, while FIG. 10 shows the electrical conductivity as observed under varying oxygen partial pressure at a constant temperature of 950° C. As explained before, it is understood from FIG. 2 that when the transition metal is Co, Fe, Ni or Cu, the conductivity is remarkably improved at least at low temperatures, by substitution of the transition metal for part of the Mg.

FIG. 10 shows that the conductivity varies depending on the oxygen partial pressure when the transition metal is Ni, Cu or Mn, but is held substantially constant at high levels, regardless of the variation of the oxygen partial pressure, when the transition metal is Co or Fe.

FIG. 5 shows the results of the measurement of the ion transference number on a compound which employs Co as the transition metal, together with electrical conductivity. The measurement of the ion transference number was conducted as follows. Oxygen partial pressure on both sides of the sample was set to different known levels by using a partition so as to form an oxygen concentration cell, and the electromotive force of this oxygen concentration cell was measured. At the same time, the theoretical electromotive force under the same conditions was determined based on Nernst's equation. Then, the ion transference number was determined as the ratio of the measured electromotive force to the theoretical electromotive force. Tendencies similar to that shown in FIG. 5 were obtained also with transition metals other than Co and the electrical conductivity increased while the ion transference number decreased, when the ratio of the transition metal to Mg increased. It is to be understood, however, the increase of the electrical conductivity is logarithmic and, hence, much greater in absolute value than the reduction in the ion transference number. Therefore, the absolute value of the oxide-ion conductivity is increased, despite the reduction in the ion transference number.

Example 2

Test pieces of oxide-ion conductor was produced from a sintered body of $La_{0.8}Sr_{0.2}Ga_{0.8}Mg_{0.115}CO_{0.085}O_{3-w}$ in the same manner as Example 1 and were subjected to measurement of electrical conductivity at varying temperature under a fixed oxygen partial pressure of $10^{-5}$ atm. The results of the measurement (Arrhenius plot of conductivity) are shown in FIG. 11.

Example 3

Test pieces of oxide-ion conductor were produced from a sintered body of $La_{1-x}Sr_xGa_{0.8}Mg_{0.115}Co_{0.085}O_{3-w}$ (x=0.1, 0.15, 0.2, 0.25 or 0.3) in the same way as Example 1 and were subjected to measurement of electrical conductivity at varying temperature under a fixed oxygen partial pressure or at a fixed temperature under varying oxygen partial pressure.

FIG. 3 shows the relationship between the value of "x" and the electrical conductivity as observed at 950° C. The Arrhenius plot of conductivity (oxygen partial pressure $10^{-5}$ atm) and the oxygen-partial-pressure dependence of the electrical conductivity (at 950° C.) are respectively shown in FIGS. 12A and 12B. It will be noted that the oxygen-partial-pressure dependence of conductivity varies according to the "x" value.

Example 4

Figure 4B:
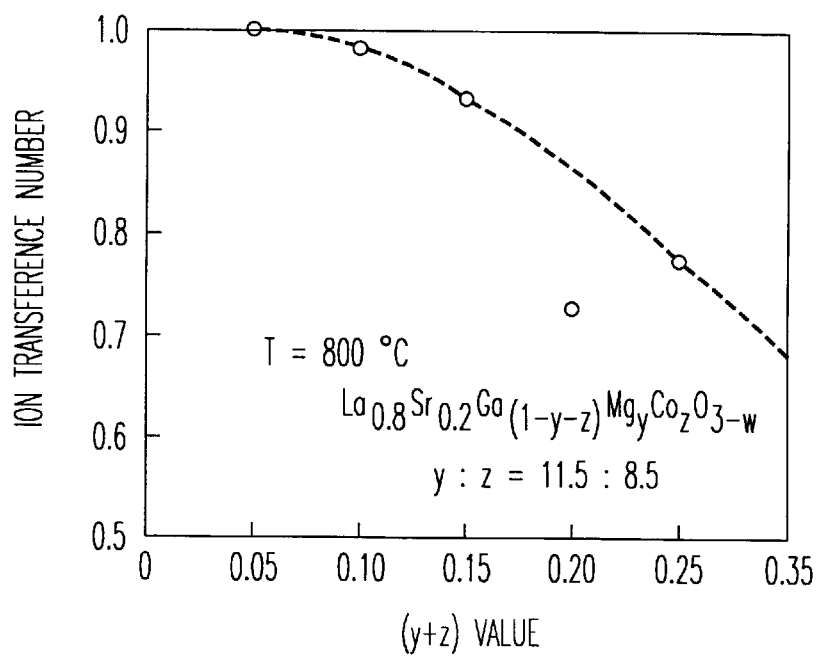
FIG. 4B is a graph showing the relationship between the ion transference number and the (y+z) value in the same oxide-ion conductor as that discussed on FIG. 4A.
Figure 4C:
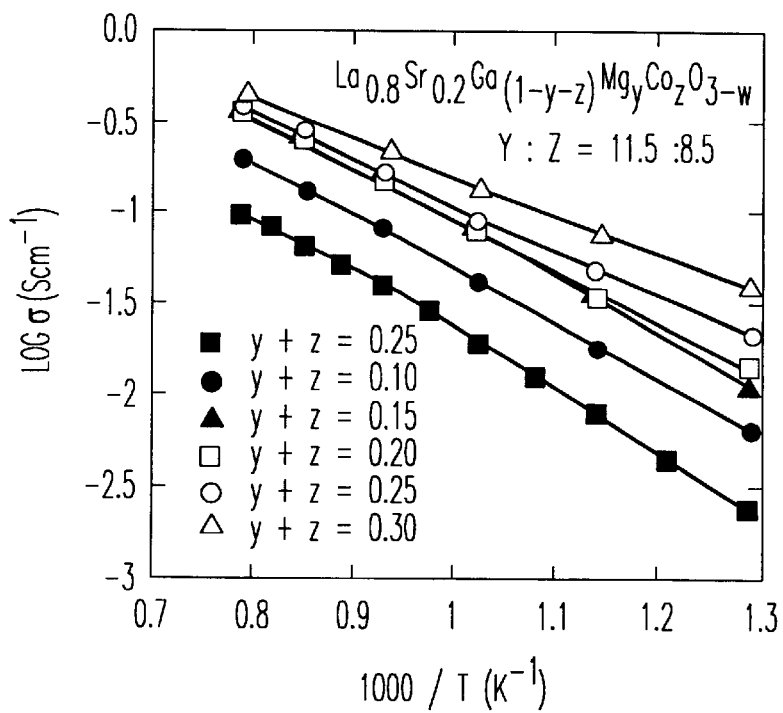
FIG. 4C is a graph showing the relationship between electrical conductivity and the temperature exhibited by the oxide-ion conductor of a 5-element compound oxide having various total atomic ratio (y+z).

Test pieces of oxide-ion conductor were produced from a sintered body of $La_{0.8}Sr_{0.2}Ga_{1-y-z}Mg_yCo_zO_{3-w}$ in the same way as Example 1 and were subjected to measurement of electrical conductivity at varying temperature. The Arrhenius plot of conductivity (oxygen partial pressure $10^{-5}$ atm) is shown in FIG. 4C. FIG. 4A shows the relationship between the value (y+z) and the electrical conductivity at 950° C., while FIG. 4B shows the relationship between the ion transference number and the electrical conductivity.

Example 5

Test pieces of oxide-ion conductor were produced from a sintered body of $Ln_{0.9}A_{0.1}Ga_{0.8}B1Co_{0.1}O_{3-w}$ in the same way as Example 1, while varying the metal atoms of Ln, A and B1, and were subjected to measurement of electrical conductivity. The conductivity values ($\sigma$/S cm$^{-1}$) under an oxygen partial pressure of $10^{-5}$ atm and at temperature of 950° C. were as follows:

(1) $Ln_{0.9}Sr_{0.1}Ga_{0.8}Mg_{0.1}CO_{0.1}O_{3-w}$: 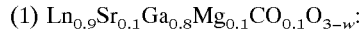
   Ln=La: 0.53
   Ln=Pr: 0.49
   Ln=Nd: 0.36
   Ln=Ce: 0.08
   Ln=Sm: 0.05

(2) $La_{0.9}A_{0.1}Ga_{0.8}Mg_{0.1}Co_{0.1}O_{3-w}$: 
   A=Sr: 0.53
   A=Ca: 0.24
   A=Ba: 0.22

3) $La_{0.9}Sr_{0.1}Ga_{0.8}B1_{0.1}Co_{0.1}O_{3-w}$: 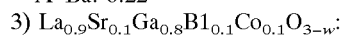
   B1=Al: 0.12
   B1=Mg: 0.53
   B1=In: 0.23

Example 6

Test pieces of oxide-ion conductor were produced from a sintered body of $La_{0.8}Sr_{0.2}Ga_{0.8}Mg_{0.2-z}Fe_zO_{3-w}$ in the same way as Example 1 and were subjected to X-ray diffraction for investigation of the crystal structure. As a result, these test pieces were confirmed to have the perovskite crystal structure.

FIG. 6 shows the results of measurement of electrical conductivity exhibited by the oxide-ion conductor of this example at 950° C. under an oxygen partial pressure of $10^{-5}$ atm. It is understood from this figure that specifically high levels of electrical conductivity can be obtained when the "z" value falls within the range of from 0.01 to 0.15. The dependence of the electrical conductivity on the temperature and on the oxygen partial pressure of the above-mentioned composition, as observed when the "z" value is 0.03, are shown in FIGS. 7A and 7B, respectively. It will be seen that this oxide-ion conductor exhibits high levels of electrical conductivity and a high ion transference number over a wide range of temperatures and oxygen partial pressures.

As will be understood from the foregoing description, the present invention provides an oxide-ion conductor that has oxide-ion conductivity higher than that of stabilized zirconia, which is the typical conventional oxide-ion conductor. Moreover, the oxide-ion conductivity exhibited by the oxide-ion conductor of the invention is still higher than that of the 4-element compound oxide that is formed by doping the A site and the B site with non-transition metals alone and, which itself exhibits higher oxide-ion conductivity than stabilized zirconia. Furthermore, the oxide-ion conductor of the invention permits free control of the ratio between the conductivity provided by oxide ions and the conductivity provided by electrons, i.e., the ion transference number. Thus, the present invention provides not only a material suitable for use as the oxide-ion conductor in the narrower sense in which the ion transference number is as high as 0.9 or greater, but also a material which can effectively be used as an electron-ion mixed conductor.

The oxide-ion conductor in accordance with the present invention, having a high ion transference number, can function at lower temperatures than the operating temperatures of stabilized zirconia, and shows high levels of oxide-ion conductivity over the entire range of oxygen partial pressures, starting from a pure oxygen atmosphere to a hydrogen atmosphere. This conductor, therefore, can suitably be used as the materials of the electrolyte of a solid oxide fuel cell, a gas sensor such as oxygen sensor, an oxygen separator membrane of an electrochemical oxygen pump, and so forth and is expected to provide excellent performance in these products compared with conventional materials. In particular, the oxide-ion conductor expressed by the formula (2) is specifically advantageous because it exhibits high levels of oxide-ion conductivity over wide ranges of temperature and oxygen partial pressure from a pure oxygen atmosphere to a substantially pure hydrogen atmosphere.

The electron-ion-mixed conductor that also falls within the scope of the oxide-ion conductor of the invention and that exhibits electron-ion-mixed conductivity can suitably be used as the material of an air electrode of a solid oxide fuel cell or a gas separator membrane that relies on a difference in gas concentrations. A solid oxide fuel cell may be formed employing this electron-ion-mixed conductor as the air electrode and, as the electrolyte, the above-mentioned oxide-ion conductor in the narrower sense exhibiting a high ion transference number. Such a solid oxide fuel cell can produce a large output power, because the electrical resistance posed by the interface can be reduced.

Obviously, additional modifications and variations of the present invention are possible in light of the above teachings. It is therefore to be understood that within the scope of the appended claims, the invention may be practiced otherwise than as specifically described herein.

The priority documents of the present application, Japanese Patent Applications Hei 9-234838, Hei 10-079583 and Hei 10-081185, filed on Aug. 29, 1997, Mar. 26, 1998, and Mar. 27, 1998, respectively, are hereby incorporated by reference.

What is claimed is:

1. An oxide-ion conductor having the formula:

$$Ln_{1-x}A_xGa_{1-y-x}B1_yB2_z \text{ oxide}$$ 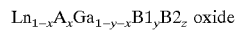

wherein
   Ln is at least one element selected from the group consisting of La, Ce, Pr, Nd and Sm;
   A is at least one element selected from the group consisting of Sr, Ca and Ba;
   B1 is at least one element selected from the group consisting of Mg, Al and In;

B2 is at least one element selected from the group consisting of Co, Fe, Ni and Cu;

x is 0.05 to 0.3;

y is 0 to 0.29;

z is 0.01 to 0.3; and y+z is 0.025 to 0.3.

2. The oxide-ion conductor of claim 1, wherein $y \geq 0.025$ and $z \leq 0.15$.

3. The oxide-ion conductor of claim 1, wherein $z > 0.15$.

4. The oxide-ion conductor of claim 1, wherein Ln is at least one element selected from the group consisting of La and Nd, A is Sr, B1 is Mg, B2 is Co, x is 0.10 to 0.25, y is 0 to 0.17, z is 0.02 to 0.15, and y+z is 0.10 to 0.25.

5. The oxide-ion conductor of claim 2, wherein Ln is La,

A is Sr,

B1 is Mg,

B2 is Fe, x is 0.1 to 0.3, y is 0.025 to 0.29, z is 0.01 to 0.15, and y+z is 0.035 to 0.3.

6. The oxide-ion conductor of claim 5, wherein x is 0.15 to 0.25, y is 0.09 to 0.24, z is 0.01 to 0.05, and y+z is 0.10 to 0.25.

7. A solid oxide fuel cell, comprising:

(a) an air electrode, (b) an electrolyte, and (c) a fuel electrode, wherein said electrolyte comprises the oxide-ion conductor of claim 2.

8. A solid oxide fuel cell, comprising:

(a) an air electrode, (b) an electrolyte, and (c) a fuel electrode, wherein said electrolyte comprises the oxide-ion conductor of claim 4.

9. A solid oxide fuel cell, comprising:

(a) an air electrode, (b) an electrolyte, and (c) a fuel electrode, wherein said electrolyte comprises the oxide-ion conductor of claim 6.

10. A solid oxide fuel cell, comprising:

(a) an air electrode, (b) an electrolyte, and (c) a fuel electrode, wherein said air electrode comprises the oxide-ion conductor of claim 3.

11. The solid oxide fuel cell of claim 7, wherein said air electrode comprises an oxide-ion conductor having the formula:

$$Ln_{1-x}A_xGa_{1-y-x}B1_yB2_z \text{ oxide}$$

wherein

Ln is at least one element selected from the group consisting of La, Ce, Pr, Nd and Sm;

A is at least one element selected from the group consisting of Sr, Ca and Ba;

B1 is at least one element selected from the group consisting of Mg, Al and In;

B2 is at least one element selected from the group consisting of Co, Fe, Ni and Cu;

x is 0.05 to 0.3;

y is 0 to 0.29;

z is >0.15 to 0.3; and y+z is >0.15 to 0.3.

12. The solid oxide fuel cell of claim 8, wherein said air electrode comprises an oxide-ion conductor having the formula:

$$Ln_{1-x}A_xGa_{1-y-x}B1_yB2_z \text{ oxide}$$

wherein

Ln is at least one element selected from the group consisting of La, Ce, Pr, Nd and Sm;

A is at least one element selected from the group consisting of Sr, Ca and Ba;

B1 is at least one element selected from the group consisting of Mg, Al and In;

B2 is at least one element selected from the group consisting of Co, Fe, Ni and Cu;

x is 0.05 to 0.3;

y is 0 to 0.29;

z is >0.15 to 0.3; and y+z is >0.15 to 0.3.

13. The solid oxide fuel cell of claim 9, wherein said air electrode comprises an oxide-ion conductor having the formula:

$$Ln_{1-x}A_xGa_{1-y-x}B1_yB2_z \text{ oxide}$$

wherein

Ln is at least one element selected from the group consisting of La, Ce, Pr, Nd and Sm;

A is at least one element selected from the group consisting of Sr, Ca and Ba;

B1 is at least one element selected from the group consisting of Mg, Al and In;

B2 is at least one element selected from the group consisting of Co, Fe, Ni and Cu;

x is 0.05 to 0.3;

y is 0 to 0.29;

z is >0.15 to 0.3; and y+z is >0.15 to 0.3.

14. The solid oxide fuel cell of claim 7, wherein said fuel electrode comprises:

(1) Ni, and (2) a compound of the formula of $Ce_{1-m}C_m$ oxide, wherein C at least one element selected from the group consisting of Sm, Gd, Y and Ca, and m is 0.05 to 0.4.

15. The solid oxide fuel cell of claim 8, wherein said fuel electrode comprises:

(1) Ni, and (2) a compound of the formula of $Ce_{1-m}C_m$ oxide, wherein C at least one element selected from the group consisting of Sm, Gd, Y and Ca, and 16. The solid oxide fuel cell of claim 9, wherein said fuel electrode comprises:
(1) Ni, and
(2) a compound of the formula of $Ce_{1-m}C_m$ oxide, wherein C at least one element selected from the group consisting of Sm, Gd, Y and Ca, and
m is 0.05 to 0.4.

17. The solid oxide fuel cell of claim 10, wherein said fuel electrode comprises:
(1) Ni, and
(2) a compound of the formula of $Ce_{1-m}C_m$ oxide, wherein C at least one element selected from the group consisting of Sm, Gd, Y and Ca, and
m is 0.05 to 0.4.

18. The solid oxide fuel cell of claim 13, wherein said fuel electrode comprises:
(1) Ni, and
(2) a compound of the formula of $Ce_{1-m}C_m$ oxide, wherein C at least one element selected from the group consisting of Sm, Gd, Y and Ca, and
m is 0.05 to 0.4.

19. A gas sensor comprising the oxide-ion conductor of claim 2.

20. A gas sensor comprising the oxide-ion conductor of claim 4.

21. A gas sensor comprising the oxide-ion conductor of claim 6.

22. An oxygen separating membrane for an electrochemical oxygen pump, comprising the oxide-ion conductor of claim 2.

23. An oxygen separating membrane for an electrochemical oxygen pump, comprising the oxide-ion conductor of claim 4.

24. An oxygen separating membrane for an electrochemical oxygen pump, comprising the oxide-ion conductor of claim 6.

25. An electrochemical oxygen pump, comprising the oxygen separating membrane of claim 22.

26. An electrochemical oxygen pump, comprising the oxygen separating membrane of claim 24.

27. A gas separation membrane comprising the oxide-ion conductor of claim 3.

28. A method of making the oxide-ion conductor of claim 1, comprising:
sintering a mixture containing Ln, A, Ga, B1 and optionally B2, to form said oxide-ion conductor.

29. A method of making the oxide-ion conductor of claim 2, comprising:
sintering a mixture containing Ln, A, Ga, B1 and optionally B2, to form said oxide-ion conductor.

30. A method of making the oxide-ion conductor of claim 3, comprising:
sintering a mixture containing Ln, A, Ga, B1 and optionally B2, to form said oxide-ion conductor.

31. A method of making the oxide-ion conductor of claim 4, comprising:
sintering a mixture containing Ln, Sr, Ga, Mg and optionally Co, to form said oxide-ion conductor.

32. A method of making the oxygen separating membrane of claim 22, comprising:
molding a mixture containing Ln, A, Ga, B1 and optionally B2, to form a molded article, and
sintering said molded article, to form said oxygen separating membrane.

33. A method of making the gas separation membrane of claim 23, comprising:
molding a mixture containing Ln, A, Ga, B1 and optionally B2, to form a molded article, and
sintering said molded article, to form said oxygen separating membrane.

34. A method of making the gas separation membrane of claim 27, comprising:
molding a mixture containing Ln, A, Ga, B1 and optionally B2, to form a molded article, and
sintering said molded article, to form said gas separation membrane.

35. A method of making the solid oxide fuel cell of claim 7, comprising:
forming a laminate of said air electrode, said electrolyte and said fuel electrode,
wherein said electrolyte is between said air electrode and said fuel electrode.

36. A method of making the solid oxide fuel cell of claim 8, comprising:
forming a laminate of said air electrode, said electrolyte and said fuel electrode,
wherein said electrolyte is between said air electrode and said fuel electrode.

37. A method of making the solid oxide fuel cell of claim 10, comprising:
forming a laminate of said air electrode, said electrolyte and said fuel electrode,
wherein said electrolyte is between said air electrode and said fuel electrode.

38. A method of making the solid oxide fuel cell of claim 11, comprising:
forming a laminate of said air electrode, said electrolyte and said fuel electrode,
wherein said electrolyte is between said air electrode and said fuel electrode.

39. A method of making the solid oxide fuel cell of claim 12, comprising:
forming a laminate of said air electrode, said electrolyte and said fuel electrode,
wherein said electrolyte is between said air electrode and said fuel electrode.

40. A method of making the solid oxide fuel cell of claim 14, comprising:
forming a laminate of said air electrode, said electrolyte and said fuel electrode,
wherein said electrolyte is between said air electrode and said fuel electrode.

41. A method of making the solid oxide fuel cell of claim 15, comprising:
forming a laminate of said air electrode, said electrolyte and said fuel electrode,
wherein said electrolyte is between said air electrode and said fuel electrode.

42. A method of making the solid oxide fuel cell of claim 16, comprising:
forming a laminate of said air electrode, said electrolyte and said fuel electrode,
wherein said electrolyte is between said air electrode and said fuel electrode.

43. A method of making the solid oxide fuel cell of claim 17, comprising:
forming a laminate of said air electrode, said electrolyte and said fuel electrode, wherein said electrolyte is between said air electrode and said fuel electrode.

* * * * *